(12) United States Patent
Calvert et al.

(10) Patent No.: US 9,874,497 B2
(45) Date of Patent: Jan. 23, 2018

(54) TRACE GAS MEASUREMENT APPARATUS FOR ELECTRICAL EQUIPMENT

(71) Applicant: General Electric Company, Schenectady, NY (US)

(72) Inventors: Christopher Raymond Calvert, Lisburn (GB); David Peter Robinson, Lisburn (GB); Aidan Owens, Lisburn (GB); Martin Duffy, Lisburn (GB)

(73) Assignee: General Electric Company, Schenectady, NY (US)

( * ) Notice: Subject to any disclaimer, the term of this patent is extended or adjusted under 35 U.S.C. 154(b) by 147 days.

(21) Appl. No.: 14/677,537

(22) Filed: Apr. 2, 2015

(65) Prior Publication Data
US 2016/0290896 A1   Oct. 6, 2016

(51) Int. Cl.
*G01N 1/14*  (2006.01)
*G01N 33/28* (2006.01)
(Continued)

(52) U.S. Cl.
CPC ............ *G01N 1/14* (2013.01); *G01N 1/2202* (2013.01); *G01N 1/2226* (2013.01); *G01N 21/01* (2013.01);
(Continued)

(58) Field of Classification Search
CPC ............ G01N 1/2226; G01N 21/3504; G01N 2001/2229; G01N 33/2841; G01N 1/14;
(Continued)

(56) References Cited

U.S. PATENT DOCUMENTS 3,779,066 A * 12/1973 Fore ................. G01N 30/12
                                              73/23.25
4,385,634 A    5/1983 Bowen et al.
(Continued)

FOREIGN PATENT DOCUMENTS

DE    19503802 C1   3/1996
DE    19833601      12/1999
(Continued)

OTHER PUBLICATIONS

European Search Report and Opinion issued in connection with corresponding EP Application No. 16161980.4 dated Jul. 21, 2016.
(Continued)

*Primary Examiner* — Natalie Huls
(74) *Attorney, Agent, or Firm* — Stephen J. Terrell; Parks IP Law LLC

(57) ABSTRACT

Provided is a trace gas measurement apparatus for electrical equipment that includes at least one sample cell configured to collect an oil sample from the electrical equipment. The sample cell having an oil receiving portion for receiving an oil sample, at least one perforated or porous sheet within a head space thereof for receiving the oil sample from the oil receiving portion, housing the oil sample thereon, and separating a new oil sample received from an existing oil sample within the at least one sample cell. The trace gas measurement apparatus also includes an oil pump for selectively pumping oil into and out of the sample cell, and a control module controlling operation of the oil pump, to adjust an oil level and air pressure within the sample cell, for performing an extraction process of trace gases within the oil sample.

20 Claims, 11 Drawing Sheets

(51) Int. Cl.
*G01N 21/01* (2006.01)
*G01N 21/3504* (2014.01)
*G01N 1/22* (2006.01)

(52) U.S. Cl.
CPC ..... *G01N 21/3504* (2013.01); *G01N 33/2841* (2013.01); *G01N 2001/2229* (2013.01); *G01N 2201/06113* (2013.01)

(58) Field of Classification Search
CPC ................ G01N 1/2202; G01N 21/07; G01N 2201/06113
See application file for complete search history.

(56) References Cited

U.S. PATENT DOCUMENTS

| | | | | |
|---|---|---|---|---|
| 4,890,478 | A * | 1/1990 | Claiborne | G01N 33/2841 73/19.11 |
| 4,944,178 | A * | 7/1990 | Inoue | G01N 33/2841 73/19.1 |
| 5,339,672 | A * | 8/1994 | Spicar | G01N 33/2841 210/188 |
| 5,400,641 | A * | 3/1995 | Slemon | G01N 1/26 706/20 |
| 5,633,711 | A | 5/1997 | Nelson et al. | |
| 5,749,942 | A * | 5/1998 | Mattis | B01D 19/0031 95/46 |
| 6,289,716 | B1 | 9/2001 | Lindgren et al. | |
| 6,391,096 | B1 | 5/2002 | Waters et al. | |
| 6,742,384 | B2 | 6/2004 | Avila | |
| 7,040,138 | B2 | 5/2006 | Braesel et al. | |
| 8,028,561 | B2 * | 10/2011 | Herz | G01N 33/2841 73/19.12 |
| 8,196,448 | B2 | 6/2012 | Kuebel et al. | |
| 8,395,777 | B2 | 3/2013 | Rao | |
| 2003/0172716 | A1 * | 9/2003 | Braesel | G01N 33/2841 73/19.1 |
| 2009/0308246 | A1 | 12/2009 | Mahoney et al. | |
| 2010/0077828 | A1 | 4/2010 | Herz et al. | |
| 2011/0246088 | A1 | 10/2011 | Santos | |
| 2012/0291521 | A1 * | 11/2012 | Cavallini | G01N 33/2841 73/19.1 |
| 2013/0247647 | A1 | 9/2013 | Mahoney et al. | |
| 2014/0053626 | A1 | 2/2014 | Jeffrey et al. | |
| 2014/0165704 | A1 | 6/2014 | Maity et al. | |
| 2014/0176936 | A1 | 6/2014 | Van Mechelen et al. | |
| 2014/0273261 | A1 | 9/2014 | Panella et al. | |
| 2016/0054286 | A1 * | 2/2016 | Van Mechelen | G01N 33/2841 436/144 |
| 2016/0231303 | A1 | 8/2016 | Park et al. | |
| 2016/0282323 | A1 * | 9/2016 | Robinson | G01N 33/2841 |

FOREIGN PATENT DOCUMENTS

| | | |
|---|---|---|
| EP | 1790965 | 5/2007 |
| EP | 2746747 | 6/2014 |
| JP | S60253842 A | 12/1985 |
| WO | 2010042178 | 4/2010 |
| WO | 2012135012 | 10/2012 |
| WO | 2013116799 | 8/2013 |

OTHER PUBLICATIONS

European Search Report and Opinion issued in EP Application No. 16161512.5 dated Jul. 21, 2016.

* cited by examiner

# US 9,874,497 B2

TRACE GAS MEASUREMENT APPARATUS FOR ELECTRICAL EQUIPMENT

I. TECHNICAL FIELD

The present invention relates generally to trace gas measurement apparatus. In particular, the present invention relates to extracting trace gases from insulating oil in electrical equipment.

II. BACKGROUND

Trace gas in electrical equipment is typically generated from electrical insulating oil used in electrical equipment, which generates and distributes electrical power. Some examples of electrical equipment include transformers, tap-changers and circuit breakers. When a fault occurs within the electrical equipment a trace gas (i.e., a fault gas) may be generated in the electrical insulating oil. The trace gases are extracted from an oil sample obtained from the electrical equipment and measured by a measurement device. The trace gas measurements are used to provide an operational and health status of the electrical equipment.

For example, in a transformer, when faults e.g., arcing and overheating occur, gases such as methane and carbon dioxide or carbon monoxide are present in the insulating oil of the transformer. Measurements of these trace gases can be used to determine the type and the severity of the faults which occur in the electrical equipment.

A measurement device such as a photo-acoustic spectroscopy are typically used to obtain trace gas measurements where small vibrations of the molecules in trace gases are generated when subjected to a particular infrared (IR) frequencies of light. In conventional methods, the trace gas extraction process may be a difficult and time-consuming process.

III. SUMMARY OF THE EMBODIMENTS

The various embodiments of the present disclosure are configured to provide trace gas measurement apparatus having a sample implementing an extraction process including performing continuous sampling, to minimize equalisation time of the trace gases.

In one exemplary embodiment, a trace gas measurement apparatus is provided. The trace gas measurement apparatus for electrical equipment that includes at least one sample cell configured to collect an oil sample from the electrical equipment. The sample cell having an oil receiving portion for receiving an oil sample, at least one perforated sheet or porous sheet within a head space thereof for receiving the oil sample from the oil receiving portion, housing the oil sample thereon, and separating a new oil sample received from an existing oil sample within the at least one sample cell. The trace gas measurement apparatus also includes an oil pump for selectively pumping oil into and out of the sample cell; and a control module controlling operation of the oil pump, to adjust an oil level and air pressure within the sample cell, for performing an extraction process of trace gases within the oil sample.

In another exemplary embodiment, a method of extracting trace gases in insulating oil of electrical equipment is provided. The method includes performing a flushing operation of the sample cell; pumping oil into the sample cell and filling the sample cell to a top surface thereof; pumping a portion of the oil out of the sample cell, and pumping new oil sample into an upper section of the sample cell; resting the new oil sample on at least one perforated sheet or porous sheet disposed within the upper section of the sample cell, adjacent to a top surface of the portion of the oil remaining therein; and adjusting air pressure within the sample cell, for extracting the trace gases.

In another exemplary embodiment, an alternative method of extracting gases in insulating oil of electrical equipment is provided. The method includes performing a flushing operation of the sample cell; pumping oil into the sample cell and filling the sample cell to a certain level less than full; and adjusting air pressure within the sample cell, for extracting the trace gases.

The foregoing has broadly outlined some of the aspects and features of various embodiments, which should be construed to be merely illustrative of various potential applications of the disclosure. Other beneficial results can be obtained by applying the disclosed information in a different manner or by combining various aspects of the disclosed embodiments. Accordingly, other aspects and a more comprehensive understanding may be obtained by referring to the detailed description of the exemplary embodiments taken in conjunction with the accompanying drawings, in addition to the scope defined by the claims.

IV. DESCRIPTION OF THE DRAWINGS

Figure 1:
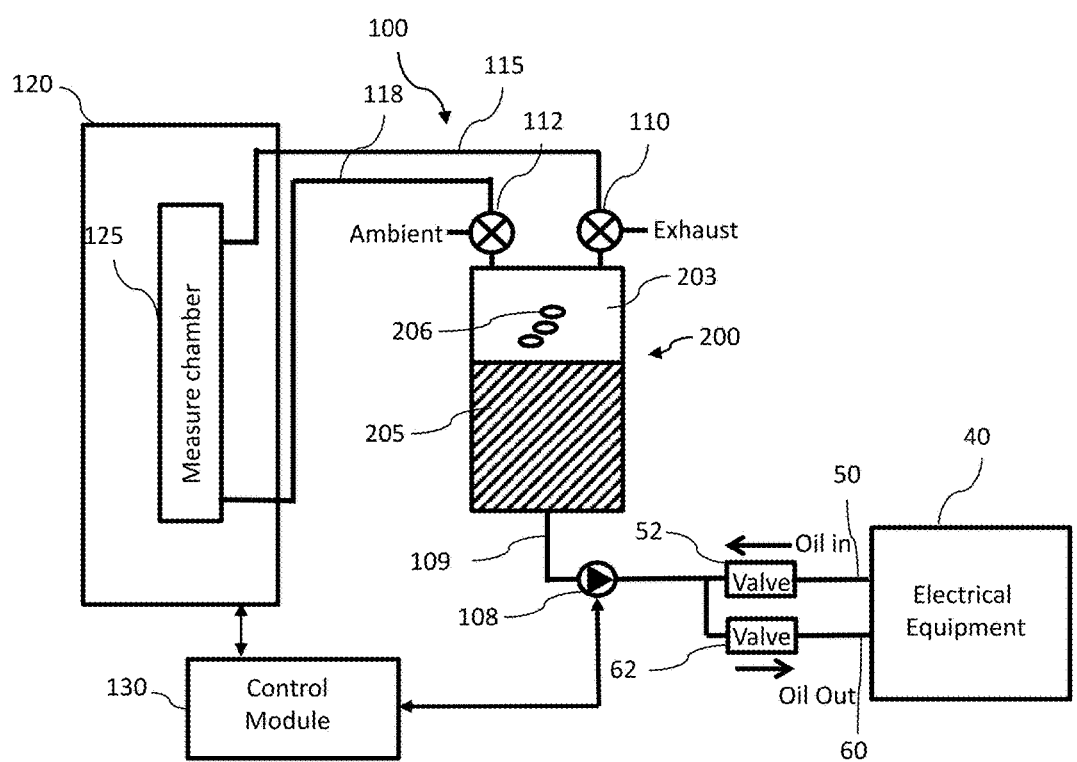
FIG. 1 is a block diagram illustrating a trace gas measurement apparatus that can be implemented within one or more embodiments of the present invention.

The drawings are only for purposes of illustrating preferred embodiments and are not to be construed as limiting the disclosure. Given the following enabling description of the drawings, the novel aspects of the present disclosure should become evident to a person of ordinary skill in the art. This detailed description uses numerical and letter designations to refer to features in the drawings. Like or similar designations in the drawings and description have been used to refer to like or similar parts of embodiments of the invention.

V. DETAILED DESCRIPTION OF THE EMBODIMENTS

As required, detailed embodiments are disclosed herein. It must be understood that the disclosed embodiments are merely exemplary of various and alternative forms. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods that are known to those having ordinary skill in the art have not been described in detail in order to avoid obscuring the present disclosure. Therefore, specific structural and functional details disclosed herein are not to be interpreted as limiting, but merely as a basis for the claims and as a representative basis for teaching one skilled in the art.

Exemplary embodiments of the present invention provides a trace gas measurement apparatus for performing dissolved gas analysis (DGA) on electrical insulating oil flowing within electrical equipment (e.g., transformers, circuit breakers, or tap changers). The trace gas measurement apparatus may be implemented within a portable gas analyzer (PGA). The DGA process is used to determine the health (e.g., the occurrence any faults or failure) of the electrical equipment and the current state of operation thereof. The trace gas measurement apparatus effectively performs trace gas extraction from oil supplied to the sample cell by continuously sampling of the oil and adjusting the surface area (i.e., head space) using perforated sheets within the sample cell and by adjusting the air pressure level. Therefore, the extraction methods of the present invention provide the advantages of decreasing the equalisation time and increasing the amount of trace gases extracted.

FIG. 1 is a block diagram illustrating a trace gas measurement apparatus that can be implemented within one or more embodiments of the present invention. As shown in FIG. 1, the trace gas measurement apparatus 100 is connectable to and communicates directly with electrical equipment 40. This communication may be performed in real-time, on-line during operation of the electrical equipment 40. The trace gas measurement apparatus 100 may be disposed in direct contact with the electrical equipment 40 or in a remote location while maintaining communication with the electrical equipment 40. The present invention is not limited to the trace gas measurement apparatus 100 being disposed in any particular location, the location may be any location suitable for the purposes set forth herein. Further, the present invention is not limited to the electrical equipment including any particular type or number of electrical equipment components (e.g., transformers, tap changers, and/or circuit breakers), and may vary accordingly.

The trace gas measurement apparatus 100 includes at least one sample cell 200 corresponding to and connectable to the electrical equipment 40, and including a head space 203 and an oil sample 205 housed therein. The sample cell 200 collects the oil sample 205 of insulating oil flowing through the electrical equipment 40, from which trace gases 206 are to be extracted for analysis. A laser-based sensor or other sensor system may be employed for receiving the trace gases from the sample cell 200 and performing the trace gas detection process, to determine the health of the electrical equipment 40. For example, an infrared (IR) absorption based technology system including a laser and a photodiode may be used.

The trace gas measurement apparatus 100 further includes an oil pump 108 connected with the sample cell 200 for selectively pumping oil into or out of the sample cell when necessary, via forward and return oil flow lines 50 and 60 connecting to the electrical equipment 40. The forward and return oil flow lines 50 and 60 respectively including valves 52 and 62, for controlling the flow of oil to the oil pump 108 from the electrical equipment 40, and from the oil pump 108 to the electrical equipment 40.

According to embodiments, the oil pump 108 is a reversible type oil pump for selectively reversing the operation thereof, to either pump oil into or out of the sample cell 200. The oil pump 108 is not limited to any particular type of reversible pump. Further, alternatively, separate pumps may be used to separately pump oil into and out of the sample cell 200. Any pump(s) suitable for the purpose set forth herein may be employed.

Further, the valves 52 and 62 are non-reversible valves (NRVs) which prevent oil being supplied from the electrical equipment 40 or to the electrical equipment 40 from reversing in direction and causing damage to the extraction process. The present invention is not limited to any particular type or number of valves, any type or number of valves suitable for the purpose set forth herein may be employed.

Further, a plurality of valves 110 and 112 within respective forward and return gas paths 115 and 118 are provided. The forward and return gas paths 115 and 118 connect the sample cell 200 to an analysis module 120, for performing measurements and analysis on trace gases 206 extracted within the sample cell 200.

The analysis module 120 includes a measure chamber 125 for receiving trace gases 206 therein, and performing dissolved gas analysis (DGA). A control mechanism (not shown) may be provided for controlling the stop and start of flow and amount of flow within the forward and return paths 115 and 118.

A control module 130 is also provided in communication with the analysis module 120, and oil pump 108 and controls operations within the trace gas measurement apparatus 100.

Further as shown, the oil sample 205 in the sample cell 200 is supplied via the forward flow line 50 from the electrical equipment 40 to the sample cell 200 during operation of the trace gas measurement apparatus 100. The oil sample 205 resides in the sample cell 200 for a predetermined period of time during which a measurement and analysis operation is to be performed. Although a single sample cell 200 is provided, a plurality of sample cells 200 may be provided to accommodate multiple electrical equipment components as needed. Alternatively, multiple electrical equipment components may be connected to a single sample cell 200.

FIGS. 2A through 2D are detailed schematics of a sample cell 200 which may be employed within the trace gas measurement apparatus 100 of FIG. 1, illustrating operations thereof that can be implemented within one or more embodiments of the present invention.

Figure 2A:
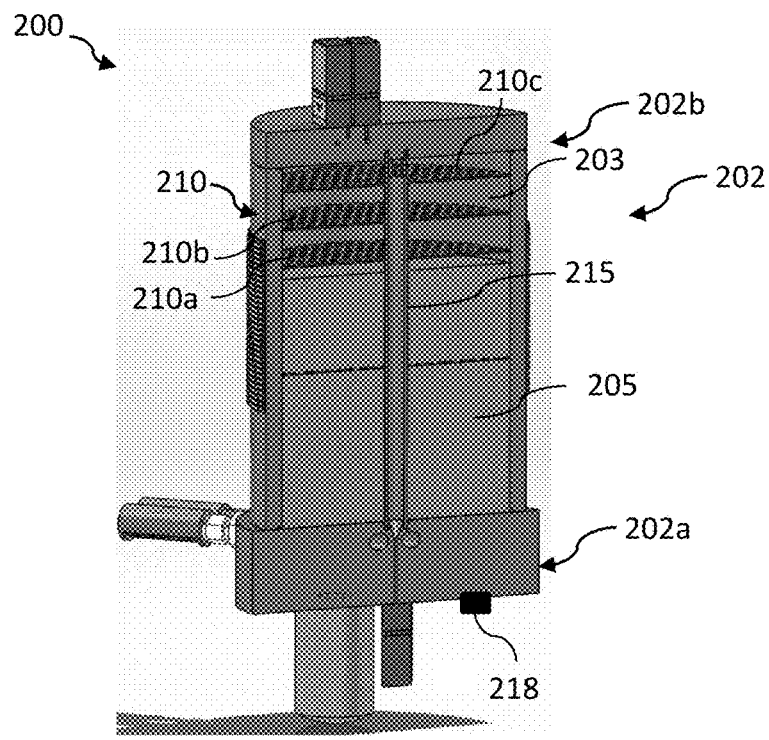
FIGS. 2A through 2D are detailed schematics of a sample cell of the trace gas measurement apparatus of FIG. 1, illustrating operations thereof that can be implemented within one or more embodiments of the present invention.

As shown in FIG. 2A, the sample cell 200 comprises a housing 202 having a lower section 202a and an upper section 202b, for housing an oil sample 205 therein. The oil sample 205 enters the sample cell 200 through an opening in the lower section 202a. The sample cell 200 further includes a plurality of perforated sheets or porous sheets 210 including 210a, 210b and 210c disposed in a fixed horizontal manner by a fixing means (not shown) within the upper section 202b of the housing 202 in the head space region 203. The perforated sheets 210 are spaced a predetermined distance apart.

According to embodiments of the present invention, the position and the predetermined distance apart of each perforated sheet 210 can be determined by several different factors. For example, the position of the highest perforated sheet 210c can be at the reduced oil level that allows the air volume within the measure chamber 125 and connecting piping to achieve the air pressure required (e.g., approximately 0.3 bar absolute), using the lowest volumetric ratio (i.e., ratio of oil-to-air volume).

The lowest perforated sheet 210a can be placed using the same criteria as that above, but applying the highest volumetric ratio to be achieved, starting the oil level before draw down at a lower level will then expand the ratio of oil-to-air volume, and hence a lower final position once the air pressure is achieved. To increase the surface area of the perforated sheets 210 to be coated with oil, more perforated sheets 210 can be placed above the highest placed sheet 210c. To decrease mixing of existing and new oil samples, additional perforated sheets 210 can be placed below the highest sheet 210c at a regular or irregular interval to below the position of the lowest perforated sheet 210a as described above.

An oil receiving portion 215 extends in a vertical direction through the housing 202, and receives new oil samples from the electrical equipment 40 via line 109 as depicted in FIG. 1. According to an embodiment, the oil receiving portion 215 may be in the form of a tube or piping for receiving and transmitting oil to the sample cell 200. A separate oil output portion 218 is also included in the sample cell 200 for outputting existing oil samples from the sample cell 200. The inputting of new oil samples and outputting of existing oil samples is controlled by the control module 130 (as depicted in FIG. 1).

Figure 2B:
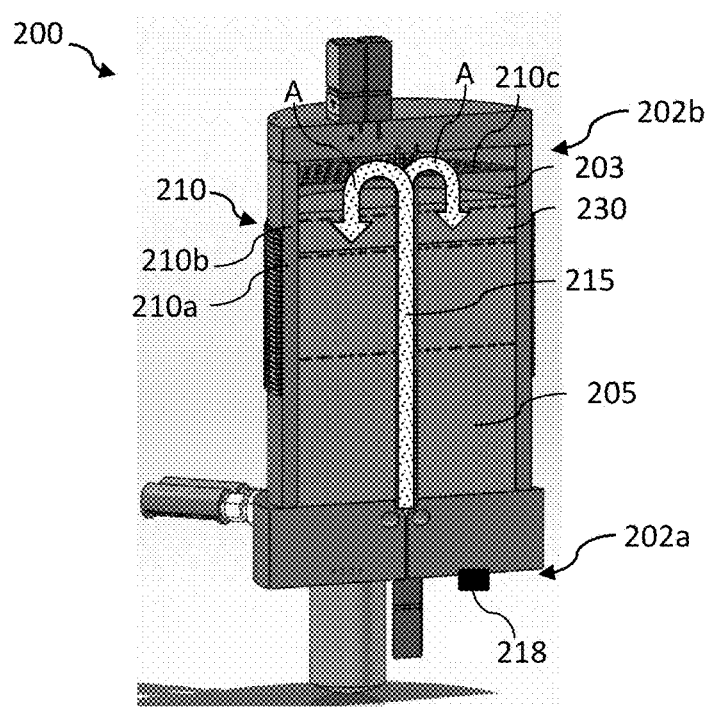
Figure 2C:
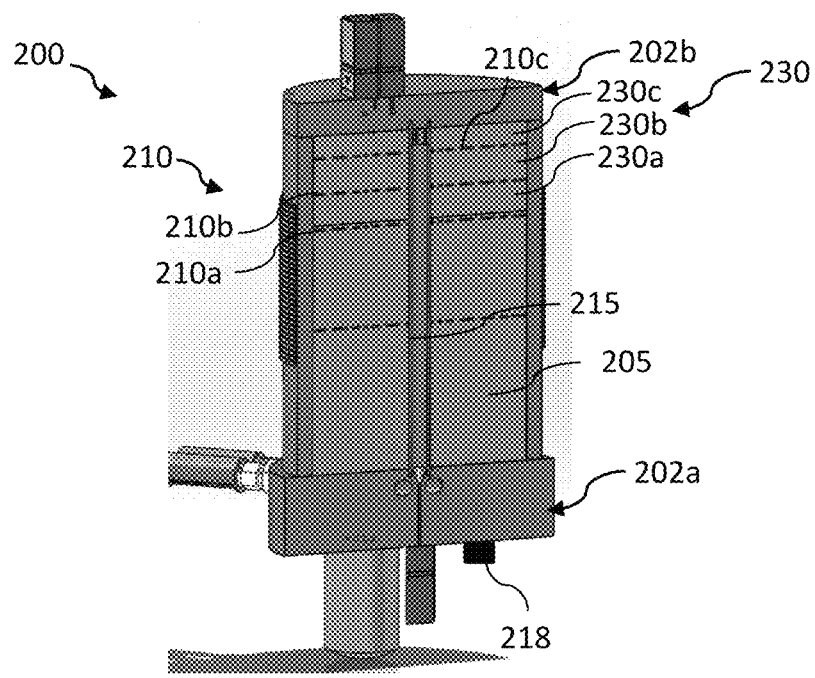
Figure 2D:
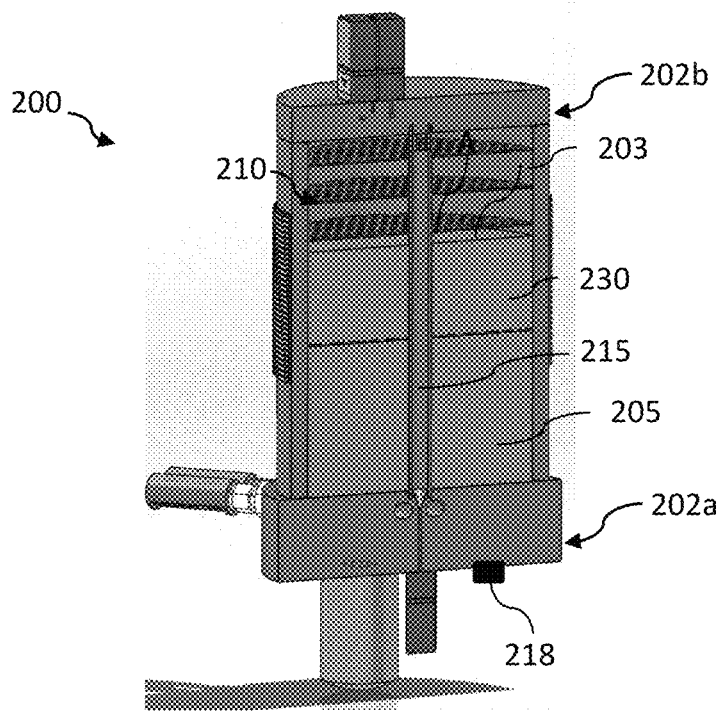

As shown in FIGS. 2B through 2D, in operation of the sample cell 200, valve 52 (as depicted in FIG. 1) is open to allow an oil sample 205 from the electrical equipment 40 to be drawn and pumped via the oil pump 108 into the sample cell 200. When a new oil sample 230 is desired during the measurement process, oil portions 230a, 230b and 230c (as depicted in FIG. 2C) of the oil sample 230 are pumped successively via the oil pump 108 through the oil receiving portion 215 and into the upper section 205b (see arrows 'A') and are disposed on the first, second and third perforated sheets 210a, 210b and 210c.

Further as shown in FIG. 2B, when the oil sample 230 is pumped into the sample cell 200, the oil level rises over the perforated sheets 210 and when the oil level is dropped the perforated sheet 210 is coated with a thin film of oil on the upper and bottom side of the sheet increasing the surface area for extracting the trace gases. As shown in FIG. 2C, the surface area (i.e., the head space 203 as depicted in FIG. 2B) for the extraction process is minimized since the oil level is at its maximum level.

The perforated sheets 210 prevent the new oil sample 230 from mixing and recirculation with the existing oil sample 205. The present invention is not limited to any particular number, thickness or type of perforated sheets and may vary accordingly. For example, the perforated sheets may be formed of any porous medium such as ceramic disc, steel wool, etc. For example, the perforated sheets may be bent perforated sheets (e.g., an upturned U shape) arranged in a circular form or a stack of perforated sheets as shown in FIG. 2A.

Next in FIG. 2D, when the trace gases 206 as depicted in FIG. 1 are to be extracted, the existing oil sample 205 is pumped out from oil output portion 218 in the lower section 202a of the housing 202, leaving the new oil sample 230, closest to the oil surface in the sample cell 200. Then, the oil remaining in the sample cell 200 is equalised, to thereby obtain trace gases 206 (as depicted in FIG. 1). The process is repeated multiple cycles by adding new oil sample 230 and pumping out existing oil sample 205 and extracting trace gases 206 (as depicted in FIG. 1) from the oil sample remaining in the sample cell 200. The oil pump 108 as depicted in FIG. 1, provides a volume pressure which further assist in extracting gas from the oil samples 205, 230.

The present invention provides the advantage of being able to extract an increased amount of trace gases at a faster rate of time. According to one or more embodiments, when multiple cycles are used, a sequence is formed that allows a progressive rate of extraction, which is dependent on a number of factors including surface area of the perforated sheets, oil and/or air pressure drop, oil type, pumping rate, and temperature, etc.

However, in testing without using additional surface area of the perforated sheets, and driving down to 0.7 bar, this resulted in approximately 6.5% of the final concentration of trace gases extracted after 1 minutes, after 8 minutes there was approximately 49% of the final concentration of trace gases (2 cycles), and after 17 minutes (4 cycles), there was approximately 67% of the final concentration. Each additional perforated sheet (approximately 65% open area) increases the surface area by approximately 70% (35% coating on top & bottom surfaces) dependent on the open area and thickness of the perforated sheets, thereby expediting the extraction process.

Additional details regarding the extraction process will be discussed below with reference to FIGS. 3A through 3F, and 4A through 4E.

Figure 3A:
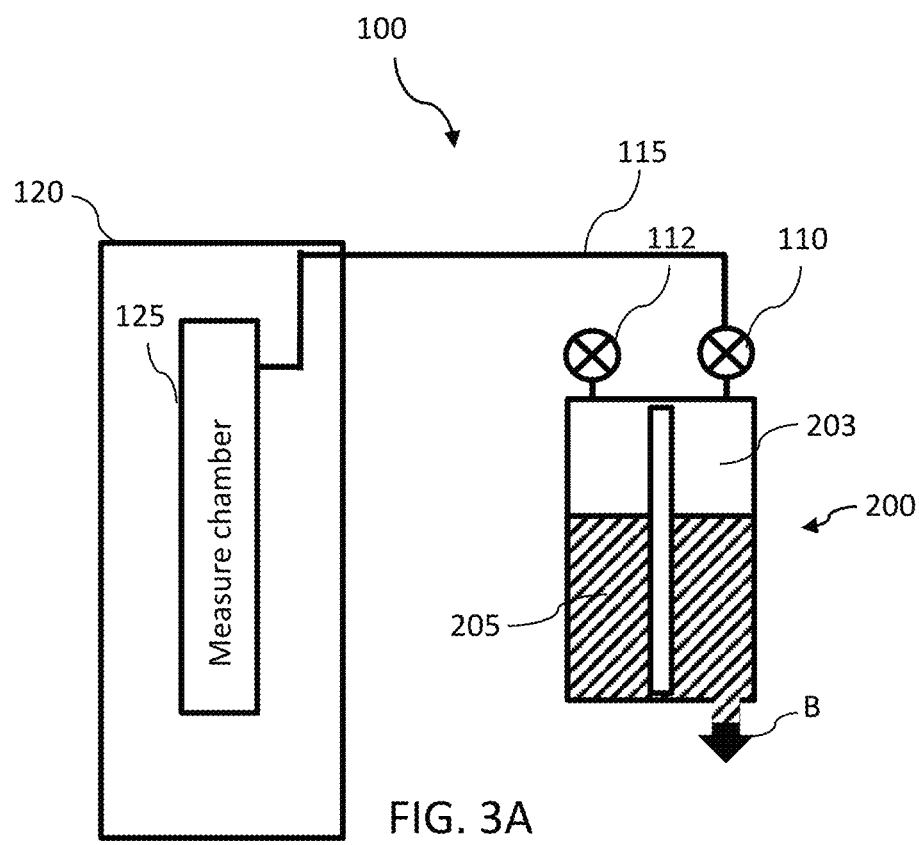
FIGS. 3A through 3F are block diagrams of the trace gas measurement apparatus of FIG. 1, illustrating trace gas extraction operations thereof that can be implemented within one or more embodiments of the present invention.

FIGS. 3A through 3F are block diagrams of the trace gas measurement apparatus of FIG. 1, illustrating trace gas extraction operations thereof that can be implemented within one or more embodiments of the present invention. As shown in FIG. 3A, at the initiation of the extraction process, a flushing operation is performed by inputting a new ambient gas sample (i.e., atmospheric air sample) which contains an amount of trace gases into the apparatus 100 via the valve 112. The oil level is dropped in the sample cell 200 is dropped by pumping the oil out (as depicted by arrow 'B') and the valve 112 is opened to receive the air sample, and air within the measure chamber 125 is also drawn into the sample cell 200 via the valve 110.

Figure 3B:
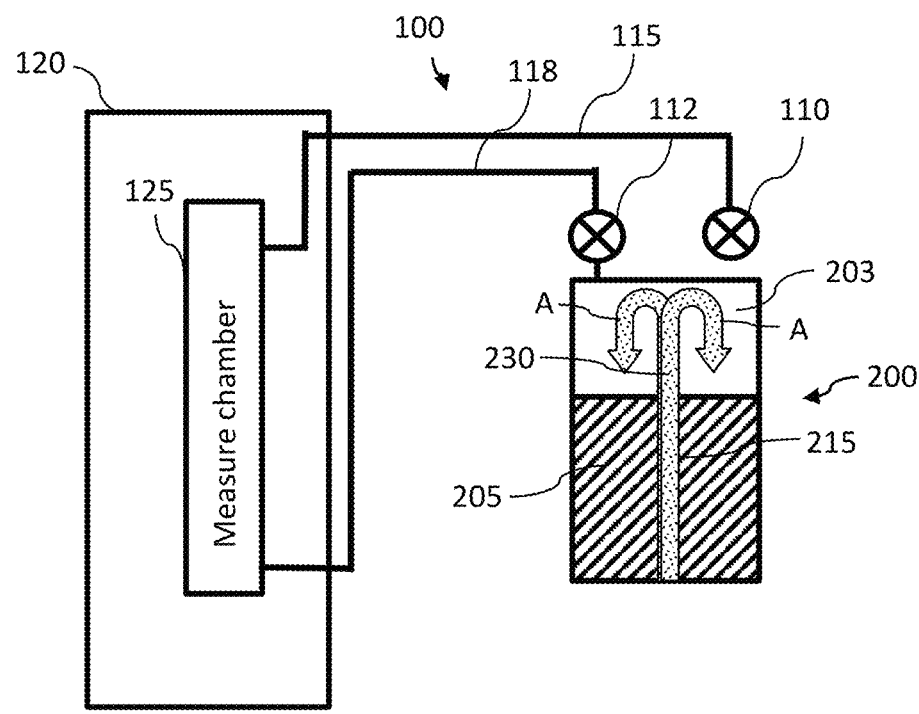

After measuring the trace gases (not shown) within the air sample, to exhaust the air sample, valve 110 is opened, air is pushed out through the valve 110 by filling the oil level with new oil 230 as shown in FIG. 3B (see arrows 'A').

Figure 3C:
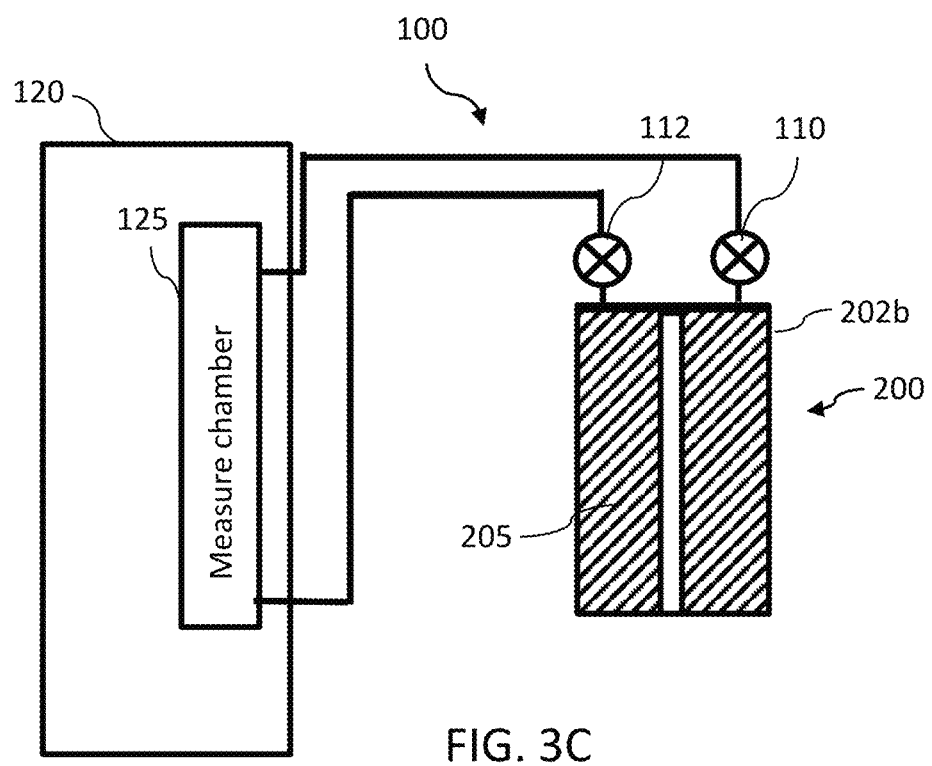
Figure 3D:
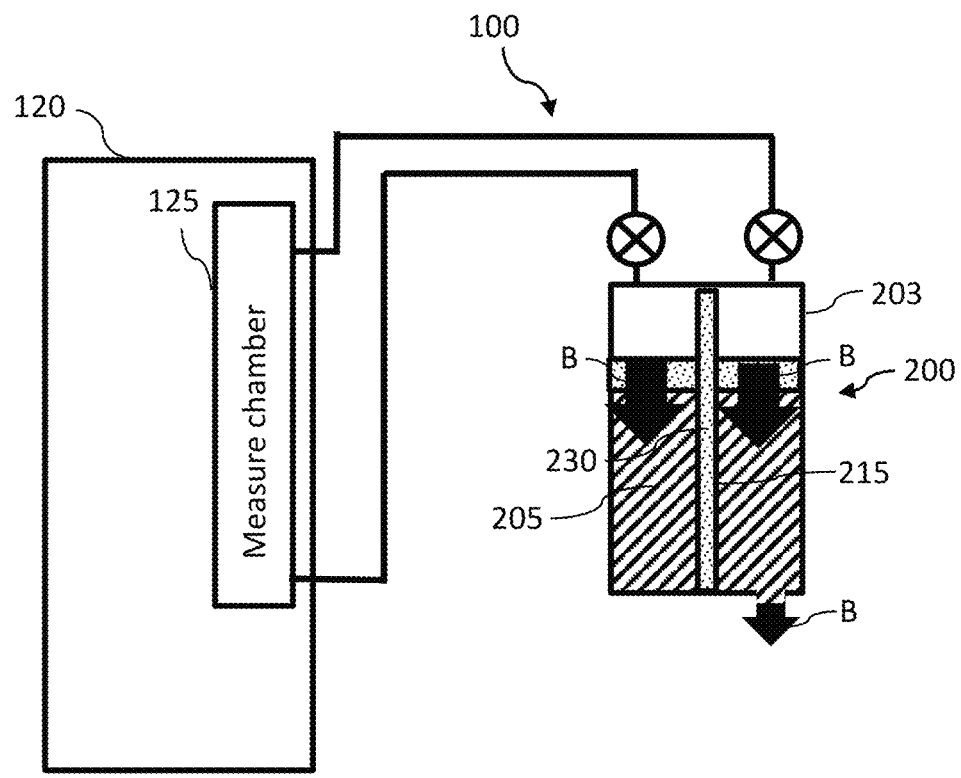
Figure 3E:
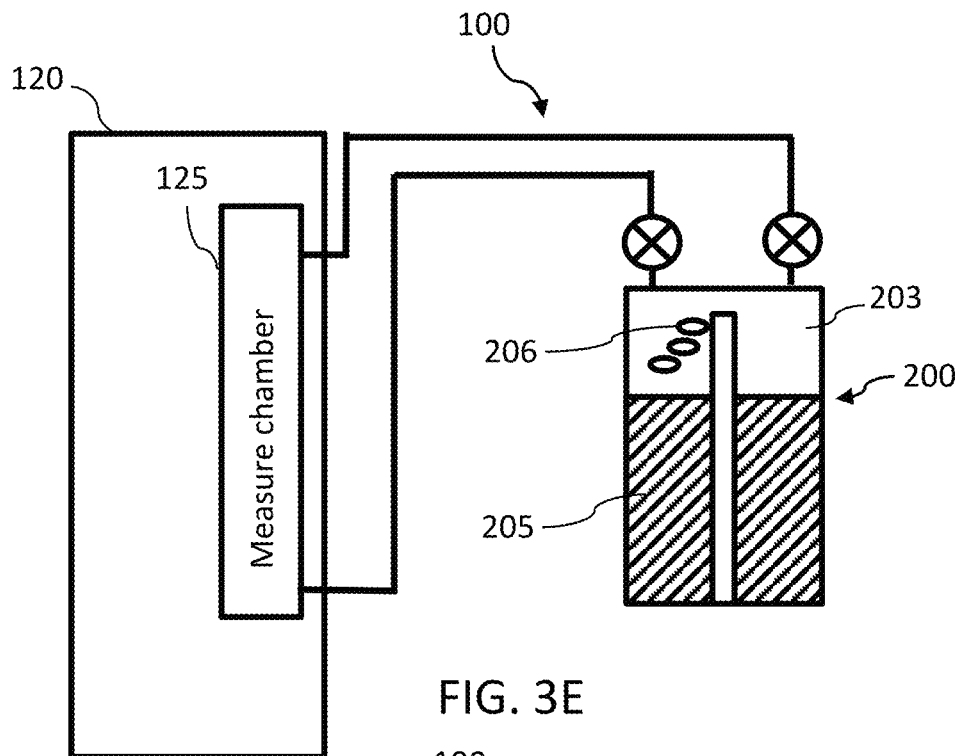

As shown in FIG. 3C, to initiate the extraction process, the sample cell 200 is filled to a top surface with oil from oil sample 205 and the valves 110 and 112 are closed. Next, in FIG. 3D, the oil is pumped from the sample cell 200 via the oil output portion 218 as depicted in FIG. 2D (see arrows 'B'), and new oil sample 230 is input into the sample cell 200, and the air pressure is dropped to approximately 0.3 bar absolute inside the sample cell 200. In FIG. 3E, the trace gases 206 are measured. According to alternative embodiments of the present invention, the air pressure may be dropped for multiple cycles within a range of 0.8 bar to 0.5 bar, and then take a measurement at approximately 0.3 bar.

Figure 3F:
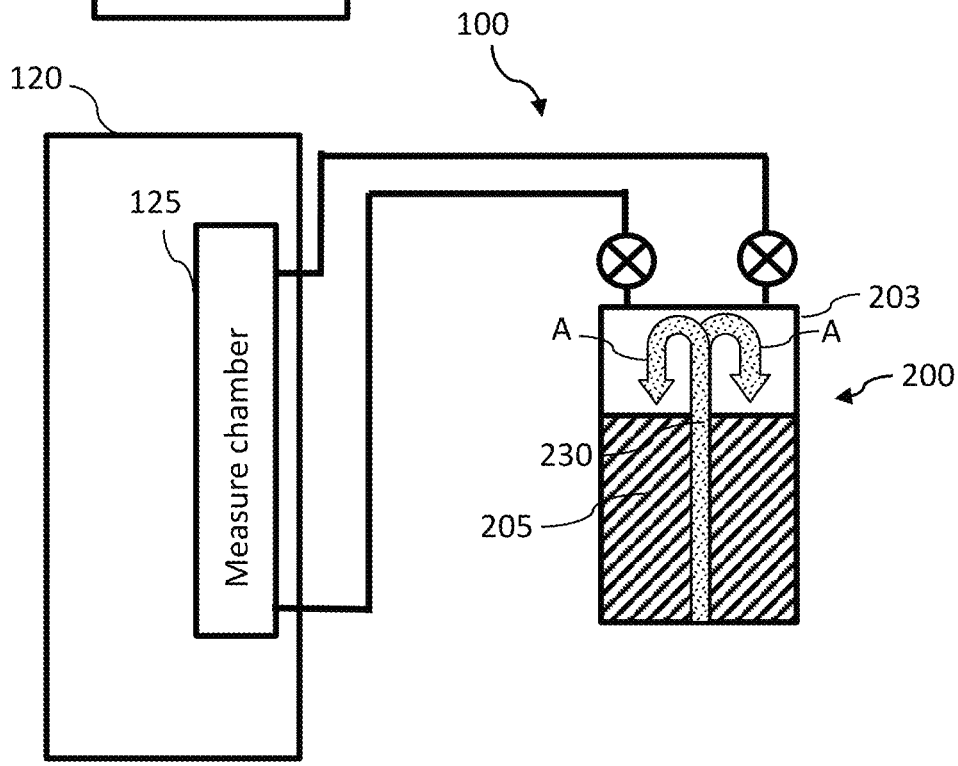

Next in FIG. 3F, more new oil sample 230 is input into the sample cell 200 via the oil receiving portion 215 (see arrows 'A') and the sample cell 200 is filled to the top surface again with oil as shown in FIG. 3C, and the process is then continuously repeated multiple cycles, to allow trace gases to be extracted from the oil in the sample cell 200 as desired. The extraction process as shown in FIGS. 3A through 3F is for a lower detection limit (LDL) for detecting trace gases such as approximately 1 ppm (parts per million).

FIGS. 4A through 4E will describe an extraction process for a higher detection limit (HDL) of approximately 50,000 ppm that can be implemented within one or more alternative embodiments of the present invention.

As an alternative extraction process from that shown in FIGS. 3A through 3F, in FIGS. 4A through 4E, the measuring parameters are adjustable. The measuring parameters include the starting oil level and the air pressure within the sample cell 200. The measuring parameters are not limited hereto and may include other parameters suitable for the purpose set forth herein.

Figure 4A:
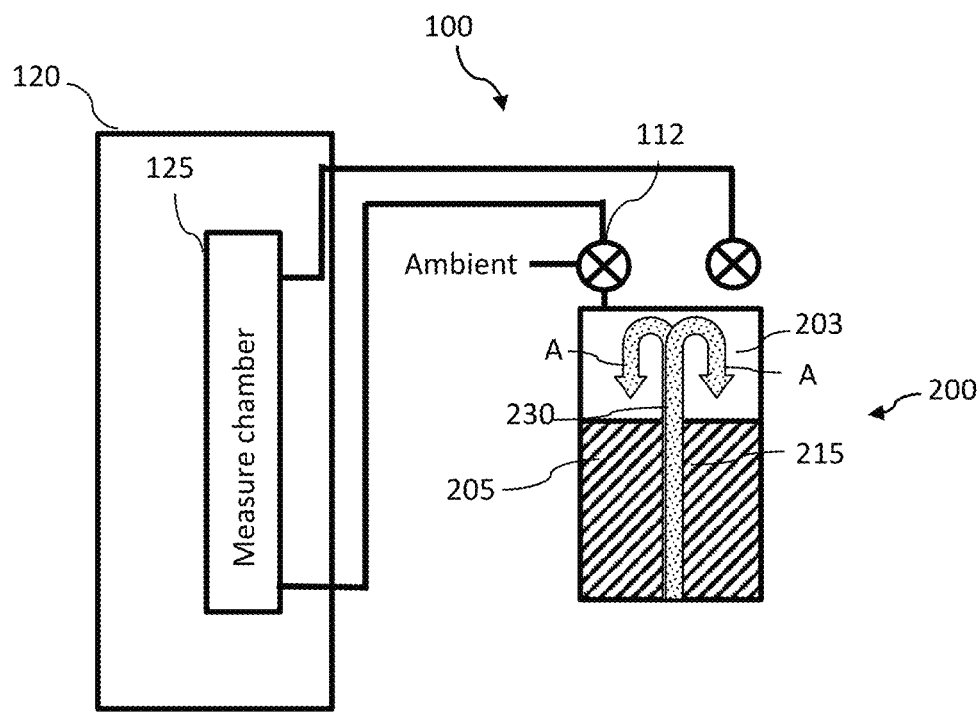
FIGS. 4A through 4E are block diagrams of the trace gas measurement apparatus of FIG. 1, illustrating trace gas extraction operations thereof that can be implemented within one or more alternative embodiments of the present invention.
Figure 4B:
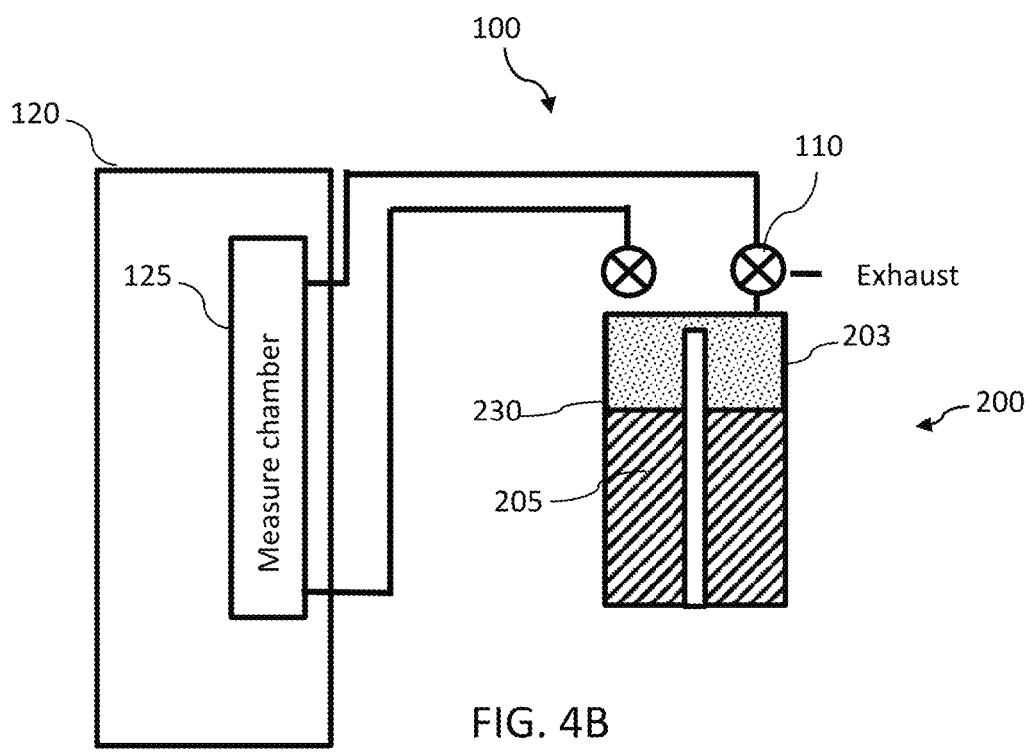
Figure 4C:
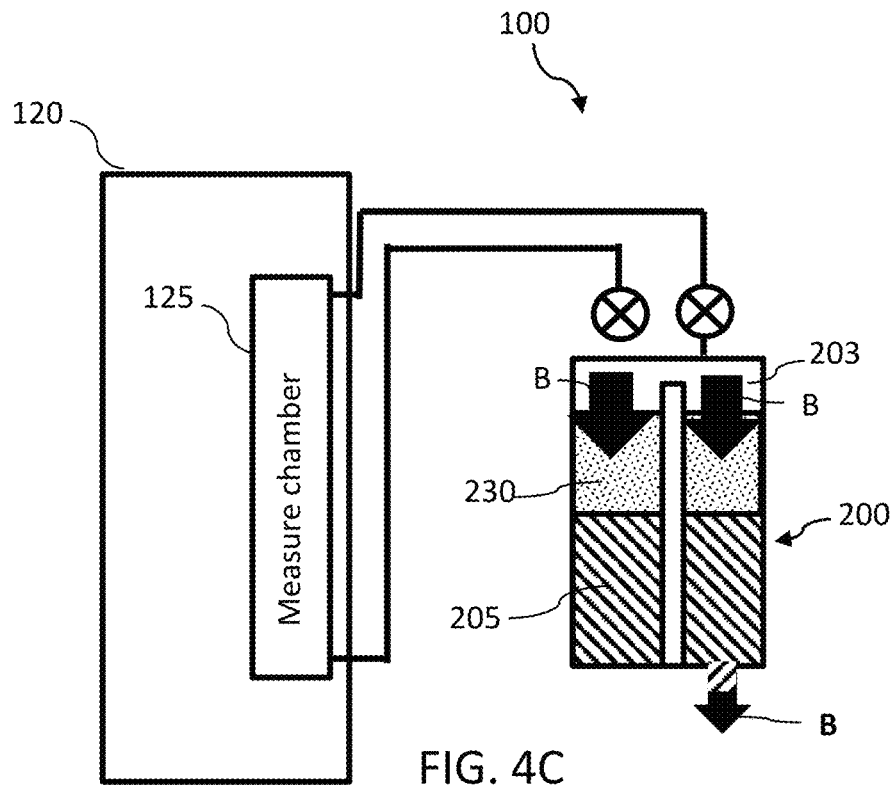

Prior to initiating the extracting process, the sample cell 200 is prepared similar to that shown in FIGS. 3A and 3B, thus, the preparation process is the same in FIGS. 4A and 4B, and detailed description thereof is omitted. A flushing operation is performed by receiving an ambient air sample in the sample cell 200 in FIG. 4A; and the sample cell 200 is filled with oil as shown in FIG. 4B, to exhaust the ambient air sample out via the valve 110. The extraction process according to this alternative embodiment begins at FIG. 4C, where the oil level within the sample cell 200 is adjusted to a certain level less than full, such as half or three-fourths by pumping oil out of the sample cell 200 via the oil pump 108 depicted in FIG. 1. In this embodiment, more air space is allotted at the top of the sample cell 200 in the head space 203.

Figure 4D:
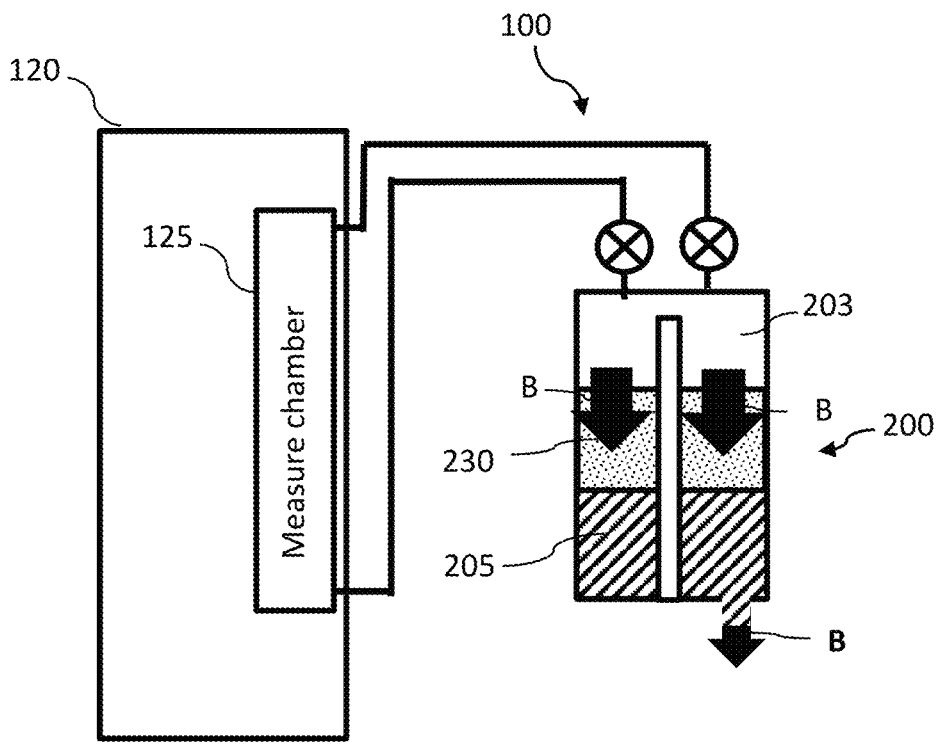
Figure 4E:
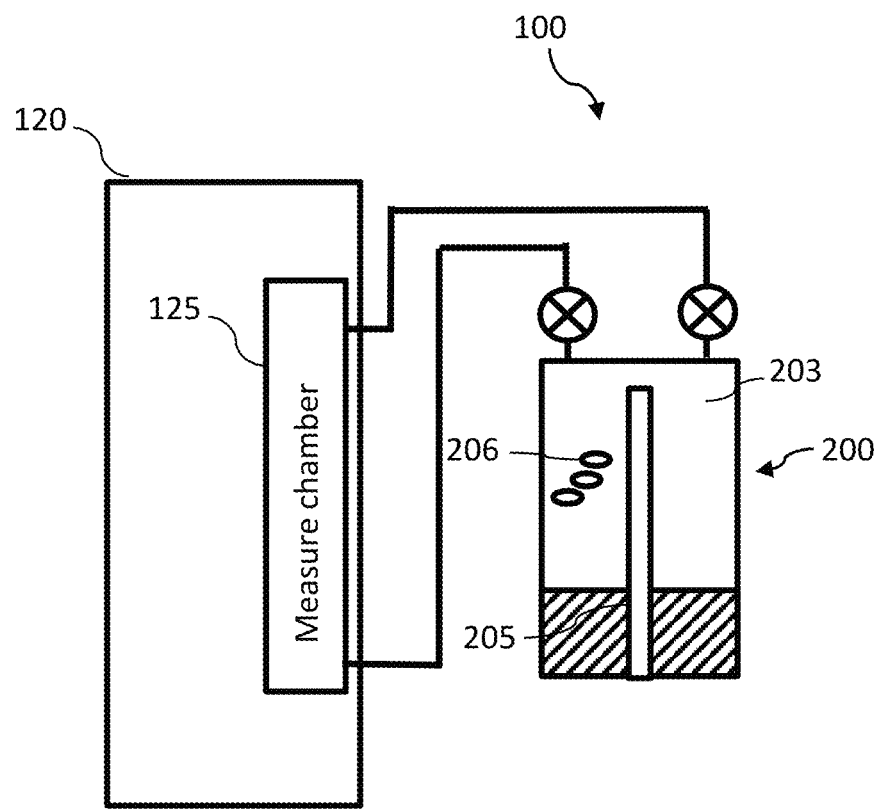

Next, as shown in FIG. 4D, the air pressure is dropped to approximately 0.3 bar, and as shown in FIG. 4E, the trace gases 206 are extracted at the adjusted parameters. The present invention is not limited to the parameters including any particular oil level or drop in air pressure and may vary as necessary to be able to extract the amount of trace gases desired.

As mentioned, the extraction processes are performed under the control of the control system 130 as shown in FIG. 1. The control module 130 includes a microcontroller or microprocessor programmed with computer software for controlling the extraction process and performing analysis of the trace gases 206 when supplied to the analysis module 120. The control module 130 controls the operation of the analysis module 120 and the oil pump 108. The control module 130 may be any type of computing device capable of performing the operations of the present invention.

Figure 5:
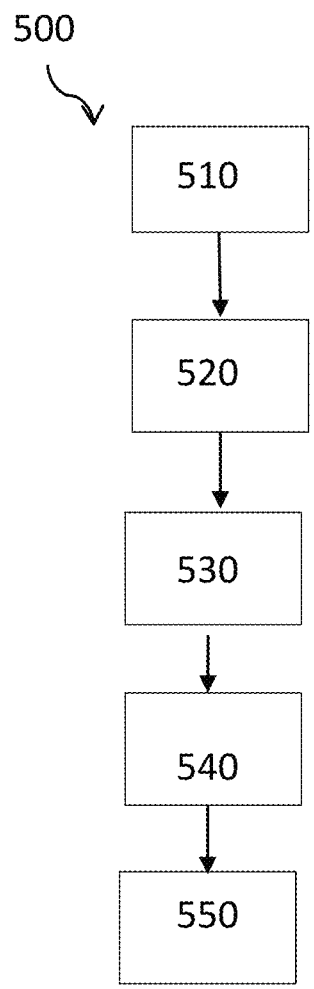
FIG. 5 is a flow diagram illustrating an exemplary trace gas extraction method illustrated in FIGS. 3A through 3F, implementing an embodiment of the present invention.

FIG. 5 is a flow diagram illustrating an exemplary trace gas extraction method 500 as illustrated in FIGS. 3A through 3F, implementing an embodiment of the present invention. The process begins at operation 510, where the oil chamber is emptied from the previous trace gases, by lowering the oil level while open to draw in ambient air, through the measure chamber, so that the system is purged (FIG. 3A).

From operation 510, the process continues to operation 520, where the measure chambers valves are closed, allowing a measurement of the trace gases within the air sample to be performed, and the air sample is then returned to the oil sample in the sample cell, via an air pump or by cycling the measure chamber valves when lowering & raising the oil level, to drive the main air circulation within the measure chamber one direction, to thereby prepare the sample cell for the extraction process (FIG. 3B).

Next, in operation 530, to initiate the extraction process the sample cell filled with oil sample and the sample cell is closed off by closing valves connected therewith (FIG. 3C), and the trace gases will be extracted. In operation, 540, some of the oil from the oil sample is pumped out of the sample cell and new oil is pumped into the sample cell (FIG. 3D). According to embodiments, the new oil portions as shown in FIG. 2C, for example, are separated by the perforated sheets fixed within the sample cell.

From operation 540, the process continues to operation 550 where the oil is further pumped out of the sample cell, and the air pressure is dropped to a predetermined amount (FIG. 3E). Then, in operation 550, the trace gases are measured.

The method 500, then returns to operation 530 (FIG. 3F) by filling the sample cell to a top surface thereof with oil, and repeating operations 530 through 550 to obtain the desired amount of trace gases for analysis.

Figure 6:
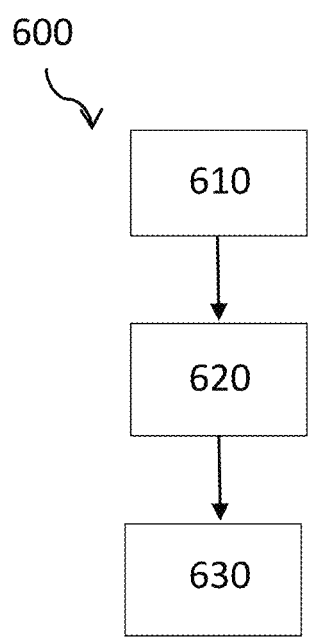
FIG. 6 is a flow diagram illustrating an exemplary trace gas extraction method illustrated in FIGS. 4A through 4E, implementing an alternative embodiment of the present invention.

FIG. 6 is a flow diagram illustrating an exemplary trace gas extraction method 600 as illustrated in FIGS. 4A through 4E, implementing an alternative embodiment of the present invention.

The method 600 begins at operation 610 where prior to initiating the extraction process, an air sample is received in the sample cell and trace gas extraction is performed on the air sample (FIG. 4A) and the sample cell is then filled with oil to exhaust the air sample out of the sample cell (FIG. 4B).

From operation 610, the process continues to operation 620 where the oil level within the sample cell is adjusted to a certain level less than full, such as half or three-fourth by pumping oil out of the sample cell using an oil pump.

Next, in operation 630, the air pressure within the sample cell is dropped to a certain level (e.g., 0.3 bar) and trace gases are extracted at the adjusted parameters (i.e., the oil level and the air pressure) for higher detection limit (HDL) of trace gases.

The measurement apparatus of the present invention may be used in an on line measurement type arrangement with electrical equipment such as a main transformer and/or tank changer. The measurement apparatus may further be implemented in real-time to determine the condition of the total electrical system (e.g., a transformer system). These faults can be detected early, to minimize cost associated with unplanned outages and any electrical equipment failure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A trace gas measurement apparatus for electrical equipment, the trace gas measurement apparatus comprising:
    a sample cell configured to collect an oil sample from the electrical equipment, wherein the sample cell comprises:
    an oil receiving portion configured to direct oil into an upper section of the sample cell;
    an oil output portion configured to direct oil out of a lower section of the sample cell;
    a perforated sheet that is positioned in the sample cell between an upper point where the oil receiving portion directs oil into the upper section of the sample cell and a lower point where the oil output portion directs oil out of the sample cell,
    wherein an oil level defines a head space in the upper section of the sample cell; and
    a forward gas path configured to direct trace gases out of the head space of the sample cell, wherein the forward gas path is above the perforated sheet;
    an oil pump for selectively pumping oil at least one of into and out of the sample cell; and a control module configured to control operation of the oil pump.

2. The trace gas measurement apparatus of claim 1, further comprising an analysis module including a measure chamber for receiving the trace gases therein and performing dissolved gas analysis, wherein the forward gas path connects the head space to the analysis module.

3. The trace gas measurement apparatus of claim 1, wherein the perforated sheet is fixed in a horizontal manner within the sample cell.

4. The trace gas measurement apparatus of claim 3, wherein the oil receiving portion extends in a vertical direction through the sample cell, and is configured to deposit the oil sample on top of the perforated sheet.

5. The trace gas measurement apparatus of claim 1, wherein the perforated sheet is configured to deter oil above the perforated sheet from commingling with oil below the perforated sheet.

6. The trace gas measurement apparatus of claim 1, wherein, the control module is configured to adjust the air pressure within the sample cell for extracting the trace gases at least in part by controlling the pump to:
fill the sample cell to a top surface thereof with oil through the oil receiving portion; and
remove oil from the sample cell through the oil output portion.

7. The trace gas measurement apparatus of claim 6, wherein the air pressure is selected from a range from 0.8 bar to 0.5 bar.

8. The trace gas measurement apparatus of claim 1, wherein the control module is configured to adjust the air pressure within the sample cell for extracting the trace gases at least in part by controlling the pump to adjust the oil level within the sample cell to a certain level less than full by pumping oil out of the sample cell through the oil output portion.

9. The trace gas measurement apparatus of claim 1, wherein the control module is configured to control at least one valve to perform a flushing operation of the head space of the sample cell.

10. The trace gas measurement apparatus of claim 9, wherein the flushing operation comprises receiving ambient air in the sample cell, measuring trace gases within the ambient air, and exhausting the ambient air from the sample cell.

11. The trace gas measurement apparatus of claim 1, wherein the perforated sheet is configured to deter comingling of oil that is received in the sample cell above the perforated sheet through the oil receiving portion with oil that is within the sample cell below the perforated sheet.

12. The trace gas measurement apparatus of claim 1, comprising a plurality of perforated sheets.

13. The trace gas measurement apparatus of claim 12, wherein the plurality of perforated sheets are horizontal and spaced apart.

14. The trace gas measurement apparatus of claim 12, wherein the oil level is configured to move from above a highest one of the plurality of perforated sheets to below a lowest one of the plurality of perforated sheets.

15. The trace gas measurement apparatus of claim 1, wherein the control module is configured to control the oil pump to coat the perforated sheet with oil by: pumping oil into the sample cell such that the oil level rises above the perforated sheet; and pumping oil out of the sample cell such that the oil level drops below the perforated sheet.

16. The trace gas measurement apparatus of claim 15, wherein the control module is configured to extract trace gasses through the forward gas path after coating the perforated sheet with oil.

17. The trace gas measurement apparatus of claim 1, wherein the oil level is configured to move above and below the perforated sheet.

18. The trace gas measurement apparatus of claim 1, wherein the perforated sheet includes one of a ceramic disc and steel wool.

19. The trace gas measurement apparatus of claim 1, wherein the perforated sheet is a bent perforated sheet.

20. The trace gas measurement apparatus of claim 19, wherein the perforated sheet has an upturned U-shape.

* * * * *